(12) United States Patent
Sirch et al.

(10) Patent No.: US 7,767,865 B2
(45) Date of Patent: Aug. 3, 2010

(54) METHOD FOR PRODUCING HYDROXYPIVALALDEHYDE AND NEOPENTYL GLYCOL

(75) Inventors: Tilman Sirch, Schifferstadt (DE); Michael Steiniger, Neustadt (DE); Steffen Maas, Bubenheim (DE); Stefan Rittinger, Mannheim (DE); Stephan Schlitter, Shanghai (CN)

(73) Assignee: BASF SE (DE)

( * ) Notice: Subject to any disclaimer, the term of this patent is extended or adjusted under 35 U.S.C. 154(b) by 0 days.

(21) Appl. No.: 12/529,197

(22) PCT Filed: Feb. 25, 2008

(86) PCT No.: PCT/EP2008/052240
§ 371 (c)(1),
(2), (4) Date: Aug. 31, 2009

(87) PCT Pub. No.: WO2008/107333
PCT Pub. Date: Sep. 12, 2008

(65) Prior Publication Data
US 2010/0113836 A1    May 6, 2010

(30) Foreign Application Priority Data
Mar. 2, 2007  (EP) .................. 07103432

(51) Int. Cl.
C07C 45/72   (2006.01)
C07C 45/33   (2006.01)
C07C 45/75   (2006.01)
C07C 31/18   (2006.01)

(52) U.S. Cl. ............... 568/463; 568/464; 568/853
(58) Field of Classification Search ............ 568/463, 568/464, 853
See application file for complete search history.

(56) References Cited

U.S. PATENT DOCUMENTS

| 4,386,018 A | 5/1983 | Merger et al. |
| 4,386,219 A | 5/1983 | Merger et al. |
| 6,048,441 A | 4/2000 | Auer et al. |

FOREIGN PATENT DOCUMENTS

| DE | 10317545 A1 | 11/2004 |
| EP | 0044444 A1 | 1/1982 |
| EP | 0522368 A1 | 1/1993 |
| EP | 0895982 A1 | 2/1999 |
| EP | 1568678 A1 | 8/2005 |
| WO | WO 9817614 A1 | 4/1998 |

*Primary Examiner*—Sikarl A Witherspoon
(74) *Attorney, Agent, or Firm*—Connolly Bove Lodge & Hutz

(57) ABSTRACT

The preparation of hydroxypivalaldehyde is effected by aldolizing isobutyraldehyde with formaldehyde and subsequently working up the resulting reaction effluent by distillation, wherein the reaction effluent is fed to a distillation column which is operated at a top pressure in the range from 0.5 to 1.5 bar and in which a two-stage condensation is provided in the top region, in which the vapors are first conducted into a partial condenser operated at a temperature in the range from 50 to 80° C., whose condensate is recycled at least partly into the distillation column, and in which the vapors uncondensed in the partial condenser are fed to a downstream condenser operated at a temperature in the range from $-40$ to $+30°$ C., whose condensate is at least partly discharged.

10 Claims, 1 Drawing Sheet

METHOD FOR PRODUCING HYDROXYPIVALALDEHYDE AND NEOPENTYL GLYCOL

The invention relates to a process for preparing hydroxypivalaldehyde by aldolizing isobutyraldehyde with formaldehyde, and to a process for preparing neopentyl glycol by hydrogenating the isobutyraldehyde thus obtained.

The aldolization of isobutyraldehyde with formaldehyde and the further reaction to give neopentyl glycol are known per se. WO 98/17614 relates, for example, to a process for uninterrupted preparation of neopentyl glycol using formaldehyde which has a methanol concentration of from 0.1 to 15%. The effluent of the aldolization of isobutyraldehyde with aqueous formaldehyde is separated with the aid of octanol as an extractant into a product-of-value-containing organic phase and an aqueous phase. The organic phase is subsequently incipiently distilled in order to remove residual low boilers. The bottoms of this first column are hydrogenated, and neopentyl glycol is obtained as the product of value after a further extraction and further distillation.

Neopentyl glycol is reacted, for example, with hydroxypivalic acid to give hydroxypivalic acid neopentyl glycol ester (HPN). Such a process is described, for example, in EP-A-0 895 982.

It is an object of the present invention to provide a process for preparing hydroxypivalaldehyde by aldolizing isobutyraldehyde with formaldehyde, which leads to a minimum level of thermal stress on the product and, with low complexity, allows a virtually complete removal of the aldehyde from the aqueous solution.

BRIEF DESCRIPTION OF THE DRAWINGS

The single FIGURE shows a schematic of the distillation work-up of an aldolization reaction product.

DETAILED DESCRIPTION

Figure 1:
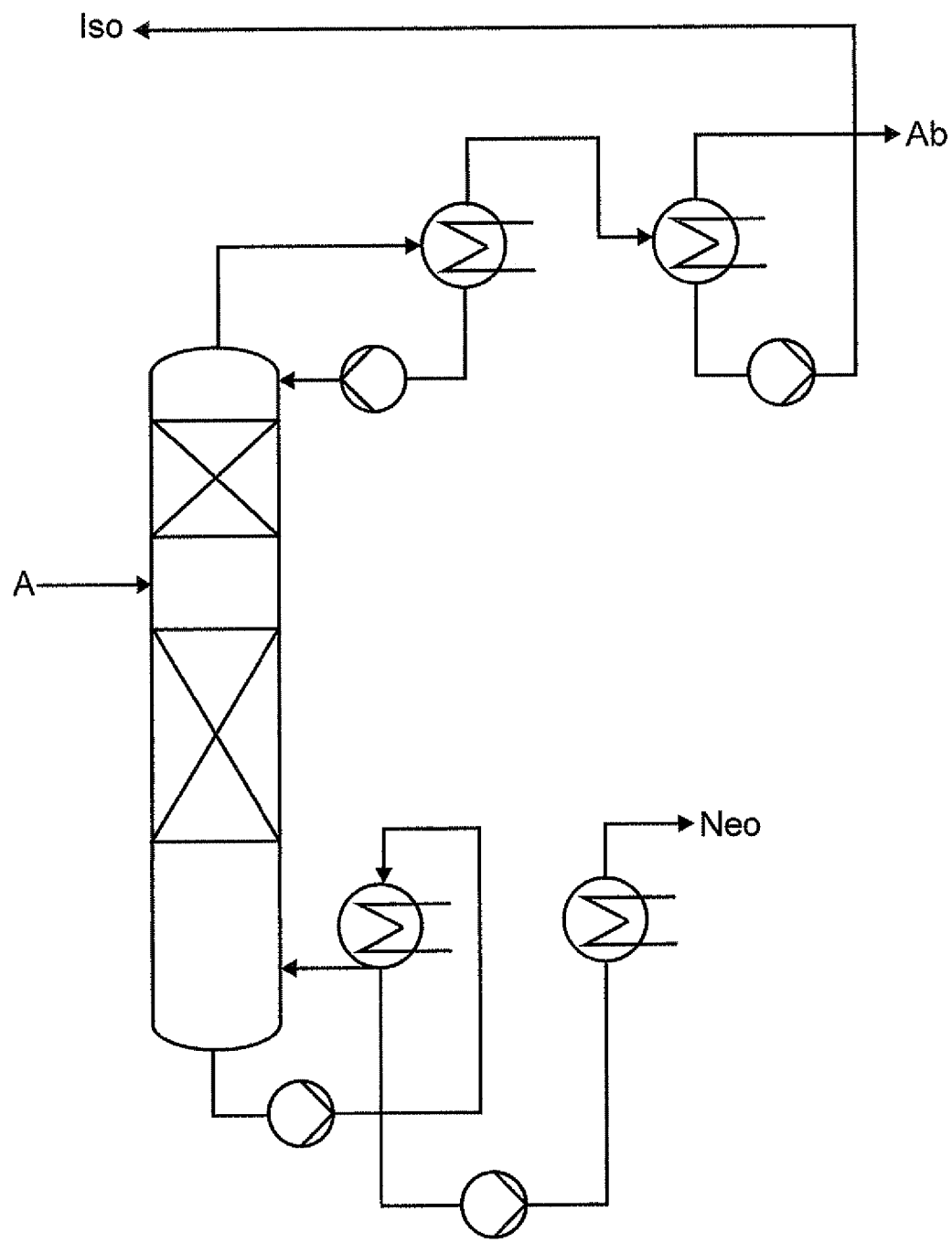

The object is achieved in accordance with the invention by a process for preparing hydroxypivalaldehyde by aldolizing isobutyraldehyde with formaldehyde and subsequently working up the resulting reaction effluent by distillation, which comprises feeding the reaction effluent to a distillation column which is operated at a top pressure in the range from 0.5 to 1.5 bar and in which a two-stage condensation is provided in the top region, in which the vapors are first conducted into a partial condenser operated at a temperature in the range from 50 to 80° C., whose condensate is recycled at least partly into the distillation column, and in which the vapors uncondensed in the partial condenser are fed to a downstream condenser operated at a temperature in the range from −40 to +30° C., whose condensate is at least partly discharged.

It has been found in accordance with the invention that the precipitation of the residual vapors in the distillation is advantageously achieved by a combination of a partial condenser with downstream cold condenser. It has been found in accordance with the invention that a total condenser which is operated directly downstream of the column can be blocked by hydroxypivalaldehyde. The condenser, however, if it is to condense the vapors completely, must be operated as cold as possible. The hydroxypivalaldehyde, owing to a high amount of cold reflux, is precipitated in the column, which leads to a high thermal stress in the bottom of the column, since the evaporator has to muster this energy. In addition, the condenser can be blocked by hydroxypivalaldehyde.

The inventive method prevents the precipitation of hydroxypivalaldehyde in the condenser.

In addition, a pressure and temperature range of the column which allows hydroxypivalaldehyde to be kept in the liquid phase and the thermal stress simultaneously to be kept low is employed.

After the aldolization, unconverted aldehydes and a portion of the amine base preferably also used in the process are removed by distillation and preferably recycled. The products of the aldolization (hydroxypivalaldehyde), water, ammonium formate from the amine base and formic acid remain in the distillation bottoms. The distillative removal should preferably be effected at moderate pressure in order not to decompose hydroxypivalaldehyde to hydroxypivalic acid neopentyl glycol ester (HPN) by virtue of elevated temperature. On the other hand, the pressure should not be too low in order still to condense the isobutyraldehyde and amine base low boilers at the top, for example trialkylamine such as trimethylamine.

The distillation must not take place at excessively low pressure, since the solubility of hydroxypivalaldehyde (HPA) in the aqueous solution suddenly drops to from about 1 to 3% by weight below about 60° C., depending on isobutyraldehyde and methanol content. Methanol is entrained via the aqueous formaldehyde, which, according to the preparation conditions, comprises from about 1 to 3% by weight of methanol.

If the unconverted aldehyde is removed from the aqueous solution, methanol would also be removed in a one-stage distillation, would be recycled into the process in the aldolization via a recycle line and would be dischargeable only via a further step, for example the discharge of aldehyde with methanol.

It has been found in accordance with the invention that the above-described disadvantages can be avoided with the multistage condensation with recycling, though specific conditions have to be maintained in the distillation. One result is that methanol is retained sufficiently in the bottoms.

It has been found that, in the case of performance of the distillative separation close to ambient pressure, i.e. at a top pressure in the range from 0.5 to 1.5 bar absolute, the low boilers can be condensed with water as the cooling medium at the top. The bottom temperatures which are established in the inventive procedure still do not lead to any significant hydroxypivalaldehyde decomposition.

The condensate of the partial condenser is preferably recycled into the distillation column to an extent of more than 70% by weight, more preferably completely. In this case, the condensate is preferably recycled into the top of the column. The condensate of the downstream condenser is preferably discharged to an extent of at least 70% by weight, especially completely.

The partial condenser is operated at a temperature in the range from 50 to 80° C., preferably from 55 to 60° C. The downstream condenser is operated at a temperature in the range from −40 to +30° C., preferably from −10 to +10° C. The top pressure is more preferably from 1 to 1.2 bar.

The bottom of the distillation column is preferably connected to an evaporator with short residence time, which is operated at a temperature in the range from 90 to 130° C., more preferably from 100 to 105° C. The evaporator is more preferably a falling-film evaporator, moreover, a wiped-film evaporator or a short-path evaporator may be used with preference. What is essential is that a short residence time and hence a low thermal stress are achieved. The evaporator can be supplied with heat in a suitable manner, for example with 4 bar of steam.

Preference is given to discharging a hydroxypivalaldehyde-enriched mixture from the bottom of the evaporator. A discharge from the circulation system is also possible in accordance with the invention. To reduce the thermal stress before the further workup, this mixture can be cooled in a condenser having a condenser temperature in the range from 50 to 80° C., more preferably from 55 to 60° C. The cooled mixture may be fed to a separator and subsequently to a hydrogenation. To prepare neopentyl glycol, aldolization and workup are first effected as above, and then a hydrogenation of the hydroxypivalaldehyde thus obtained is performed.

The distillation column preferably has internals for increasing the separating performance. The reaction exchange of the aldolization is preferably fed in a spatial region between ¼ and ¾ of the theoretical plates of the distillation column, more preferably in a spatial region between ⅓ and ⅔ of the theoretical plates of the distillation column. For example, the feed can be effected somewhat above the middle of the theoretical plates (ratio 3:4).

The distillative internals may, for example, be present as a structured packing, for example as a sheet metal packing such as Mellapak 250 Y or Montz Pak, type B1-250. It is also possible for a packing with lower or increased specific surface area to be present, or it is possible to use a fabric packing or a packing with different geometry such as Mellapak 252 Y. What is advantageous in the case of use of these distillative internals is the low pressure drop and the low specific liquid holdup compared, for example, to valve trays.

In the partial condenser, the condensate obtained is predominantly water, which is preferably fed to the column fully as reflux. For example, a mixture which comprises about 10% by weight of isobutyraldehyde, about 5% by weight of amine base such as trimethylamine, about 1% by weight of hydroxypivalaldehyde and about 5% by weight of methanol, as well as water, can be obtained as condensate. The residual vapors comprise the predominant amount of isobutyraldehyde and amine base such as trimethylamine. These are condensed as far as possible in the downstream condenser. The cooling medium used here may preferably be very cold water (for example about 5° C.) or a cold mixture (for example glycol-water at, for example, −20° C.).

The appended drawing shows a schematic of the distillative workup of the aldolization reaction product. The aldolization effluent (A) is fed at the point shown in the middle of the distillation column. At the top of the column, there follows a two-stage condensation, which ultimately removes an offgas (Ab). In the column bottom, isobutyraldehyde is recycled and evaporated. Discharged hydroxypivalaldehyde is passed on to the neopentyl glycol hydrogenation (NEO). Isobutyraldehyde (ISO) is recycled from the condensation.

The invention is illustrated in detail by the examples which follow.

EXAMPLES

Aldolization of Isobutyraldehyde (IBA) with Formaldehyde

Approx. 750 g/h of isobutyraldehyde (approx. >99.5 GC area % IBA) comprising approx. 700 g/h of formaldehyde (approx. 49% formaldehyde, 1.5% methanol, remainder water) and 80 g/h of trimethylamine solution (50% TMA in water) were reacted in a two-stage stirred tank battery.

IBA Recycling Example 1

Subsequently, the solution was freed of low boilers by distillation in a column. The column (diameter 30 mm) is equipped with 2 m of fabric packing (specific surface area 500 $m^2/m^3$) in the rectifying section and 4 m of sheet metal packing (250 $m^2/m^3$). The aldolization effluent was fed above the sheet metal packing; at the top of the column, the distillate was drawn off in gaseous form at approx. 85° C. and fed to a partial condenser. It was cooled there at 55° C. by means of water. The condensate obtained here (approx. 50 g/h) was fed fully to the column; the residual vapors were fed to the post-condenser. They were condensed virtually completely at −20° C. by means of a glycol-water cold mixture. The resulting condensate (of approx. 80 g/h) was fed to the first stirred tank. In the cold trap connected downstream of the condenser, approx. 1 g/h of liquid were obtained (approx. 80% IBA, approx. 20% TMA).

The IBA removal was conducted at a top pressure of approx. 1 bar absolute. The evaporator used was a falling-film evaporator. A bottom temperature in the bottom of the column of 102° C. was established. The amount of reflux (or amount of cooling water of the partial condenser) to the column was regulated by means of the temperature in the middle of the fabric packing; a temperature of 85° C. was established.

Approx. 100 kg/h of liquid were drawn off from the bottom of the column by means of a pump. This was fed to the falling-film evaporator (consisting of an oil-heated stainless steel tube, length 2.5 m, internal diameter approx. 21 mm, wall thickness approx. 2 mm). From the bottom of the falling-film evaporator, approx. 1.5 kg/h of product with a concentration of approx. 0.3% isobutyraldehyde were drawn off. The vapors and excess liquid were fed to the column bottom. The discharged bottom product comprised approx. 70% HPA, approx. 1.5% HPN, 0.3% IBA, remainder water.

Hydrogenation of Hydroxypivalaldehyde to Neopentyl Glycol

Catalyst Activation 150 ml of a $Cu/Al_2O_3$ catalyst as described in EP 44444 were activated in a tubular reactor at 190° C. by passing over a mixture of 5% by volume of hydrogen and 95% by volume of nitrogen (total volume 50 l (STP)/h) at ambient pressure for 24 h.

Hydrogenation

The starting solution used was the mixture described above as the hydrogenation feed. Approx. 10% by weight, based on the hydrogenation feed, of a 15% aqueous solution of trimethylamine were added to the mixture. The feed thus obtained was conducted in trickle mode at $H_2$ pressure 40 bar through the reactor heated to 120° C. The hourly space velocity was 0.4 kg of HPA ($l_{cat.}$*h). A portion of the hydrogenation effluent was added again to the feed (circulation mode). The ratio of circulation to feed was 10:1. The pH of samples of the reactor effluent at room temperature was found to be 8.9.

An aqueous solution comprising approx. 69% NPG, approx. 1.8% HPN, approx. 2% isobutanol, approx. 3.5% methanol, approx. 2% TMA, remainder water, was obtained after the hydrogenation.

IBA Recycling Example 2

Under otherwise identical aldolization conditions, a condenser with cooling water (approx. 10° C.) and a downstream phase separator was used at the top of the IBA recycling. The bottom temperature of the column was adjusted to 102° C. At the top, the distillate was fed to the condenser in gaseous form. Approx. 255 g/h of liquid condensate were obtained. In the downstream phase separator, an aqueous phase of 95 g/h was removed and fed fully to the column. In addition, 135 g/h from the phase separator were fed to the first stirred tank. In order to keep the regulation temperature in the column at 85° C., 25 g/h of organic phase were additionally fed to the column. In the cold trap connected downstream of the condenser, approx. 5 g/h of liquid were obtained (approx. 80% IBA, approx. 20% TMA).

In the bottom of the falling-film evaporator, an aqueous HPA solution of approx. 1.5 kg/h comprising approx. 0.4% isobutyraldehyde and 2.6% HPN was discharged, approx. 69% HPA.

After analogous hydrogenation to that in example 1, an aqueous solution comprising approx. 68% NPG, approx. 2.8% HPN, approx. 2.1% isobutanol, 3.4% methanol, approx. 2% TMA, remainder water, was obtained.

The invention claimed is:

1. A process for preparing hydroxypivalaldehyde by aldolizing isobutyraldehyde with formaldehyde and subsequently working up the resulting reaction effluent by distillation, which comprises feeding the reaction effluent to a distillation column which is operated at a top pressure in the range from 0.5 to 1.5 bar and in which a two-stage condensation is provided in the top region, in which the vapors are first conducted into a partial condenser operated at a temperature in the range from 50 to 80° C., whose condensate is recycled at least partly into the distillation column, and in which the vapors uncondensed in the partial condenser are fed to a downstream condenser operated at a temperature in the range from −40 to +30° C., whose condensate is at least partly discharged.

2. The process according to claim 1, wherein the bottom of the distillation column is connected to an evaporator which has a short residence time and is operated at a temperature in the range from 90 to 130° C.

3. The process according to claim 2, wherein the evaporator is a falling-film evaporator, wiped-film evaporator or short-path evaporator.

4. The process according to claim 2, wherein a mixture enriched with hydroxypivalaldehyde is discharged from the bottom of the evaporator.

5. The process according to claim 4, wherein the discharged mixture, before the workup, is cooled in a condenser with a condenser temperature in the range from 50 to 80° C.

6. The process according to claim 1, wherein the distillation column has internals for increasing the separating performance and the reaction effluent of the aldolization is fed in a spatial region between ¼, and ¾ of the theoretical plates of the distillation column.

7. The process according to claim 1, wherein the condensate of the partial condenser is recycled fully into the column.

8. The process according to claim 1, wherein the condensate of the partial condenser is recycled into the top of the column.

9. The process according to claim 1, wherein the aldolization is performed in the presence of amines as a base.

10. A process for preparing neopentyl glycol by aldolizing isobutyraldehyde with formaldehyde and working up the reaction effluent by a process according to claim 1 and subsequently hydrogenating the hydroxypivalaldehyde thus obtained.

* * * * *